United States Patent [19]

De Haan

[11] Patent Number: 5,726,347
[45] Date of Patent: Mar. 10, 1998

[54] METHOD FOR MANUFACTURING AN ELEMENT FORMED BY SEMICONDUCTOR (S) AND GAS DETECTOR PROVIDED WITH SUCH A SEMICONDUCTOR

[76] Inventor: André De Haan, Avenue du 23 Août, 8, Mons, Belgium

[21] Appl. No.: 596,295

[22] PCT Filed: Aug. 11, 1994

[86] PCT No.: PCT/EP94/02698

§ 371 Date: May 3, 1996

§ 102(e) Date: May 3, 1996

[87] PCT Pub. No.: WO95/05595

PCT Pub. Date: Feb. 23, 1995

[51] Int. Cl.⁶ .................................................. G01N 27/12
[52] U.S. Cl. .................... 73/31.06; 338/224; 427/372.2
[58] Field of Search ....................... 73/31.02, 31.03, 73/31.05, 31.06; 338/34, 224; 427/126.3, 126.6, 126.5, 372.2; 437/225; 422/90, 98

[56] References Cited

U.S. PATENT DOCUMENTS

| 3,732,519 | 5/1973 | Taguchi | 338/34 |
|---|---|---|---|
| 4,001,757 | 1/1977 | Sato et al. | 73/31.06 X |
| 4,313,338 | 2/1982 | Abe et al. | 73/31.06 |
| 4,381,922 | 5/1983 | Frey et al. | 422/98 |
| 4,453,151 | 6/1984 | Leary et al. | 338/34 |
| 5,248,617 | 9/1993 | De Haan | 73/23.2 X |
| 5,618,496 | 4/1997 | Hasumi et al. | 73/31.06 X |

*Primary Examiner*—Michael Brock
*Attorney, Agent, or Firm*—Birch, Stewart, Kolasch & Birch, LLP

[57] ABSTRACT

Process for manufacturing a semiconductor element, particularly for a flue gas detector, wherein two or more different substances, at least one of which is a semiconductor in insoluble powder form, are dispersed in powder form in a solvent, and the heterogenous suspension of the semiconductor material thus obtained is applied in granular form to an insulating substrate with a specific resistivity value of at least $10^{12}$ Ω cm.

14 Claims, 2 Drawing Sheets

METHOD FOR MANUFACTURING AN ELEMENT FORMED BY SEMICONDUCTOR (S) AND GAS DETECTOR PROVIDED WITH SUCH A SEMICONDUCTOR

The present invention is directed to a method for manufacturing an element formed by semiconductor(s) to be used for detecting a gas produced by combustion, according to which at least two substances of different composition, of which at least one is a semiconductor in a powder state, are dispersed in the state of powders insoluble in a solvent to obtain a heterogeneous suspension wherein the granular state of the semiconductor substance is maintained. The heterogenous suspension is applied on an insulating substrate having a specific resistivity value of at least $10^{12}$ $\Omega$ cm, said solvent being eliminated after application of the suspension.

Such a method is known from the U.S. Pat. No. 4,381,922. According to the known method, a mixture of semiconductor powders composed of metallophthalocyanines which are organic semiconductors is prepared. These powders are poured into an organic solvent in order to modify their initial phthalocyanine structure. In order to form the element formed by semiconductor(s), the suspension thus obtained is applied on an insolating substrate provided with the necessary electrical contacts.

Such elements formed by semiconductors are used in combustion gas detectors, such as for example fire detectors or exhaust gas detectors. According to the particular choice of the type of semiconductor or of the organic semiconductor substance used, they can be rendered particularly qualified for a well determined application.

A drawback of the known semiconductors is that they present a molecular crystalline structure and that the intermolecular bonds are assured by van der Waals forces. In these circumstances, with time and even at ambient temperature, bonds can be established between the constitutive powder particles of the semiconductor powder used. This results in a natural and progressive sintering of the preparations. Over time, this phenomenon leads to a quite rapid decrease in the semiconductor's specific surface which implies a limited life span of the detectors provided with such an element formed by semiconductor(s). Indeed, the powder is dissolved in the organic solvent in order to enable the initial phthalocyanine molecular structure to be modified and to obtain a homogeneous suspension. The organic character of the deposited powders thus leads to a sintering of the phthalocyanine powder particles which provokes a decrease of the specific surface at relatively short-term. The sintering phenomenon provokes, at ambient temperature, a sticking of powders which highly reduces the sensibility to the gaseous agents of the element formed by semiconductor (s).

The object of the invention is to realise a method for manufacturing an element composed of semiconductor(s) destined to a detector for gas produced by combustion having a longer life span while not limiting its applications.

To this end, a method for manufacturing an element composed of semiconductor(s) according to the invention is characterised in that the powders are not submitted to sintering and in that at least one semiconductor substance is a mineral semiconductor. The powders no longer being submitted to sintering neither during the manufacturing of the semiconductor nor in time, a substantially greater specific surface is obtained. The nature and the structure of the semiconductor barely change any more. Since different substances are used, the sintering process caused by time appears only feebly, what sensibly lengthens the life span of the semiconductor thus realised. Moreover, the mineral or organic semiconductors are generally in the state of powders deposited without sintering, what renders them totally suitable for the method according to the invention and enables a detection at ambient temperature. In thus avoiding the emergence of a sintering process, the sensibility of the captors no longer sensibly evolves over time.

A first preferred embodiment of a method according to the invention is characterised in that a mineral semiconductor of one of the n or p types is used which leads to n-p-n or p-n-p junctions by coupling with another mineral or organic semiconductor. An element formed by semiconductor(s) is thus obtained of which the characteristics can be modified in function of the choice of the type of semiconductors and their association. The particular use to which the detector is destined will determine the choice of the weighting of the semiconductors of type n, type p to be used.

Preferably, the semiconductor substances are chosen amongst tin, indium, cobalt, copper, antimony, germanium, gallium, nickel, chrome, zinc or titanium oxides. These oxides can be found at will on the market in the state of powders, what renders them particularly suitable for the application of the method according to the invention. Moreover, since there is no sintering these elements formed by semiconductors can be used at ambient temperature to detect a combustion emitted gas.

A second preferred embodiment of a method according to the invention is characterized in that a powder formed by an inert compound selected from, amongst others, alumina of silica is also dispersed in said solvent. The inert compound does not modify, on one hand, the nature and the structure of the semiconductor and, on the other hand, it contributes to maintain a great specific surface which limits the sintering effect in time. A mixture of a semiconductor in the powder state and of an inert component thus perfectly conforms with the concept of the present invention.

Preferably, before being dispersed the size grading of the semiconductor substances is reduced by grinding to less than 100 µm. This enables to obtain a certain uniformity in the dimensions of the powder particles that consequently avoids the formation of agglomerates in the mixtures and thus enables to obtain a great specific surface of the semiconductor.

A third preferred embodiment of a method according to the invention is characterised in that said suspension is applied in successive layers on the substrate, each applied layer being followed by a drying to evacuate the solvent. Several layers are thus obtained on a same substrate, which is all benefit for obtaining a great specific surface.

The invention also relates to a gas detector comprising an element formed by semiconductor(s) obtained by application of the above mentioned method. Such a detector is serially mounted with an adjustment module and is connected to a verification unit provided for detecting a fast variation in the resistive value of the element formed by semiconductor(s) and to generate an output signal after detection of such a variation. The verification unit operates the selection between slow and fast variation by control, after a certain delay, of the adjustment module by varying its impedance in such a manner that the voltage at the terminals of the element formed by semiconductor(s) remains sensibly constant upon feeble variations and this whatever the impedance of this element may be. Thus, only the relative value of the impedance of this element, and not its absolute value, intervenes in the detection. The detection of a fast variation enables to rapidly detect a change of the semiconductivity and thus the presence of a gas produced by combustion, which renders the detector highly performant.

Preferably, said adjustment module comprises a transistor and a capacitor connected in parallel, said adjustment signals being supplied at the base of said transistor. This offers a solution easily integrable.

The invention will now be described into more detail by means of the drawings amongst others. In the drawings:

FIG. 1 shows, at an enlarged scale, a semiconductor element obtained by application of the method according to the invention.

FIGS. 2, respectively 4 and 5 show the change in resistance in function of time due to the presence of a fire with flames, of a semiconductor element, according to the invention and comprising copper phthalocyanine, respectively tin oxide and indium oxide.

Figure 1:
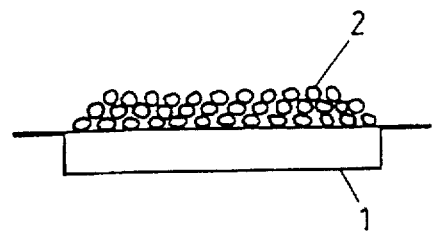

Amongst the semiconductors, semiconductors of the type n and the type p are distinguished. The properties of these semiconductors, called intrinsic semiconductors, are generally determined by the composition and the structure of the metallic oxide forming the semiconductor substance.

An extrinsic semiconductivity can however occur and in that case, it can be determined by the presence of certain gases in the atmosphere. According to the nature of the gas, the latter acts as a dopant by increasing or decreasing the number of charge carriers.

According to the presently known methods, one or more metallic oxides forming the semiconductors are used either in thin films, or in the state of powder having undergone a sintering at high temperature (about 800° C.). In consideration of the feeble value of the semiconductivity of these oxide layers and the feeble specific surfaces obtained by these techniques, the detectors thus obtained can only be used at high temperature, in a range of 450° to 600° C., in order to obtain the most adequate sensibility with respect to the application aimed at. These detectors are thus used for the detection of combustion gases such as for example $H_2$, CO, $CH_4$ and other carbon hydrides.

In the case where a mixture of powders is realised, for example barium oxide and titan oxide, and where these powders are submitted to a sintering operation at high temperature, two phenomena occur:

1/ A reaction between the barium oxide and the titan oxide which leads to the formation of barium titanate;

2/ A bond of the powder particles together by interdiffusion which leads to the formation of powder particles of larger dimension.

In this latter case, the active surface is no longer equal to the geometrical surface but corresponds to the one of the specific surface of the new formed structure, in this case that of the barium titanate.

However this specific surface is distinctly inferior to the one presented in the beginning by the used powders since they have undergone a sintering and have been bonded together by interpenetration of their crystalline network.

Another technique used to manufacture a semiconductor element is evaporation in vacuum. By this technique, a semiconductor film is obtained of which the active surface strictly corresponds to the apparent surface. This signifies that if for example, a tin oxide film is deposited, the film obtained presents an active surface strictly equal to the one of the geometrical surface.

To detect gases produced by a combustion organic semiconductors of the family of the porphyrins such as for example tetrabenzoporphyrin and metallic phthalocyanine are generally used. In most cases, it is a extrinsic semiconductivity since it is conditioned by the donor or acceptor character of the gas molecules present in the atmosphere.

However it should be noted that none of the semiconductors of mineral nature seem to have been used at ambient temperature for the detection of gas present in the atmosphere. The literature even describes that they may not be used in these conditions. The reason of this rejection is surely inherent to the production techniques and to the electronic processing of the information supplied by the detector.

The use of only one semiconductor substance to form a semiconductor element without the presence of other substances also creates a problem indeed, in time the semiconductor substance can undergo a progressive sticking. The sticking together of the powder particles provokes a decrease of the active surface and thus of the sensibility of the detector.

In order to enable the use of the detector, provided with a semiconductor element, at ambient temperature and to avoid the sintering process, the present invention proposes a manufacturing method of a semiconductor element wherein at least two different substances in the state of insoluble powder are used. At least one of these substances must imperatively be a semiconductor while the other can be composed of an inert compound or another semiconductor different from the first. The powders are not submitted to any sintering precisely in order to avoid modifying the nature and the structure of the semiconductor substances.

The used powders are preferably ground before applying them on an insulating substrate having a specific resistivity value is of at least $10^{12}$ Ω cm and whereof the resistance does not evolve with the ambient factors. The powders are ground in order to obtain a size grading is less than 100 µm. The grinding enables amongst others the dimensions of the powder particles to be the closest possible to one another.

The powders are then dispersed in a solvent, such as for example water, ethanol, acetone or a mixture of these solvents. Preferably the powder-solvent suspension is submitted to an intense agitation in order to realise a heterogeneous suspension where the different substances are well mixed and randomly distributed in the solvent. A preferential segregation or sedimentation is thus avoided. Moreover this enables to considerably reduce the probability that two powder particles of a same substance subsequently deposit next to one another on the substrate.

The suspension thus obtained is then deposited on the substrate 1 in such a manner that it is the powder particles 2 themselves, that are deposited, such as illustrated in FIG. 1. The deposit itself occurs for example by serigraphy, painting, electrophoresis or by simple immersion of the substrate in the suspension. Preferably the suspension is applied in successive layers on the substrate, each applied layer being followed by a drying in order to evacuate the solvent. The drying is for example realised by means of hot air and enables to obtain a better adherence of the deposited powder.

The adherence of the layers is obtained by insertion of the powders in the cavities due to the rugosity of the substrate used and by a form of sticking together of the powders. The used substrates are for example composed of plaquettes of sintered alumina or of oxidized silicon.

In order to enable the connection of the semiconductor element thus obtained to an electrical voltage source two electrodes are deposited on the insulating substrate, for example by serigraphy in thick layer. These electrodes are for example obtained from paste constituted either by silver-palladium alloys, either by gold or another nobel metal, which offers the advantage of avoiding corrosion phenomena or subsequent doping of the semiconductor powders.

In the case where the quality of the adherence of the powders on the carriers should be improved, they can be covered by an inert compound, insulating and porous such as, for example, a layer of plaster, of zeolite, or a porous membrane such as collodion (mixture of tetranitro and trinitro cellulose) or yet a foam composed of an organic polymer with open porosity.

The composition, the size grading and the nature of the components intervening in the mixture of the sensible layer is very important. It conditions, indeed, the base resistance of the captors, the nature of their response, their sensibility and their life span.

The base resistance of the captors depends on the resistance of each of the components taken separately and on their mutual interactions.

Thus, captors realised with the pure components present the following resistances:

| Copper phthalocyanine | $10^9$ to $10^{10}$ $\Omega$ |
|---|---|
| Indium oxide $In_2O_3$ | approx. $4 \cdot 10^4$ $\Omega$ |
| Tin dioxide $SnO_2$ | approx. $10^8$ $\Omega$ |
| Silica $SiO_2$ | insulating |
| Alumina $Al_2O_3$ | insulating |

The value of the base resistance conditions the importance of the response obtained by the detector provided with the semiconductor element. More the resistance is great, more the intensity of the variation ($\Delta R$) of the obtained signal will be great.

Figure 2:
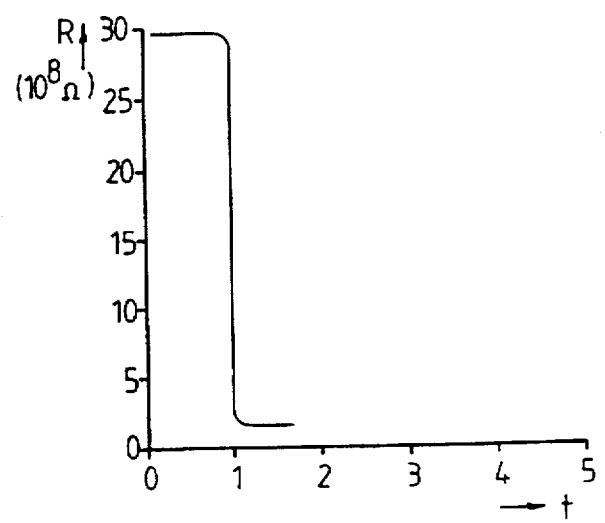

The nature of the response is directly conditioned by the semiconductivity of the used powders. Thus, a captor realised with phthalocyanine powder or with another semiconductor of the p type, sees its electrical resistance decrease upon combustion with flames, as shown in FIG. 2 where the change in the resistance R is illustrated in function of the time t1 (expressed in minutes).

In this case it is a heavy combustion where the gases produced are completely oxidized and thus present a very important electron acceptor character towards the captor.

This acceptor character provokes an increase in the number of positive charge carriers upon absorption, which increases the semiconductivity of the p type and consequently decreases the resistance.

Figure 3:
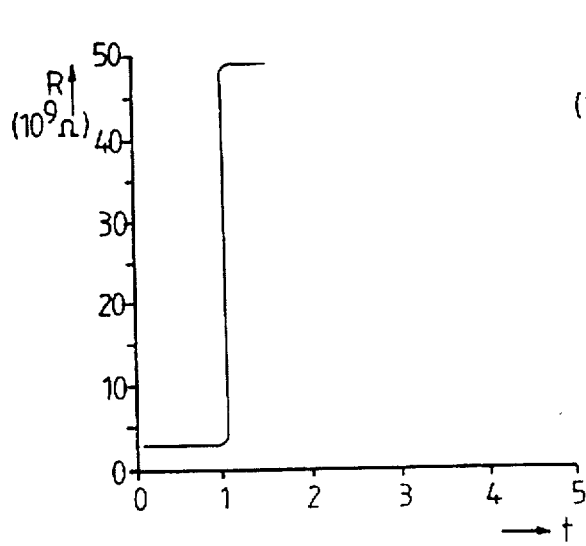
FIG. 3 shows the change in resistance in function of time due to the presence of a fire without flames of a semiconductor element, according to the invention and comprising copper phthalocyanine.

Inversely, upon a combustion without flame provoked for example by a piece of cardboard disposed on a plate heated to about 500° C., the resistance of such a captor increases very strongly, as shown in FIG. 3. Indeed, during such a combustion, the gases emitted are not completely oxidized and keep an electron donor character in respect to phthalocyanine. This donor character leads upon absorption to a great decrease of the number of positive charge carriers characteristic of a phthalocyanine of the p type. This results in a great increase in the resistance measured at the terminals of the captor.

When the semiconductor element of the n type is manufactured by using a metallic oxide such as for example tin oxide ($SnO_2$), indium oxide ($InO_3$), cobalt oxide ($CO_2O_3$), antimony oxide ($Sb_2O_3$), germanium oxide ($GeO_2$), gallium oxide ($Ga_2O_3$), tantalum oxide ($Ta_2O_3$), iron oxide ($Fe_2O_3$), tungsten oxide ($WO_3$), zinc oxide ($ZnO$) or titan oxide ($TiO_2$) the behaviour is completely inverted.

Since these powders present a semiconductivity of the n type the presence of an acceptor gas provokes a decrease in the number of negative charge carriers and thus an increase in the resistance of the captor.

Figure 4:
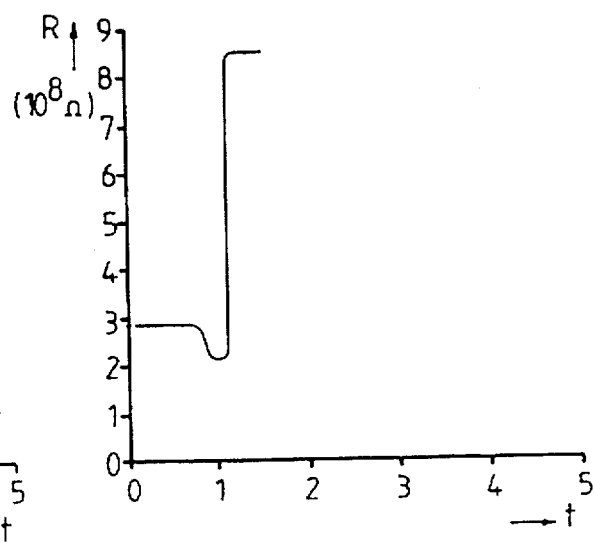
Figure 5:
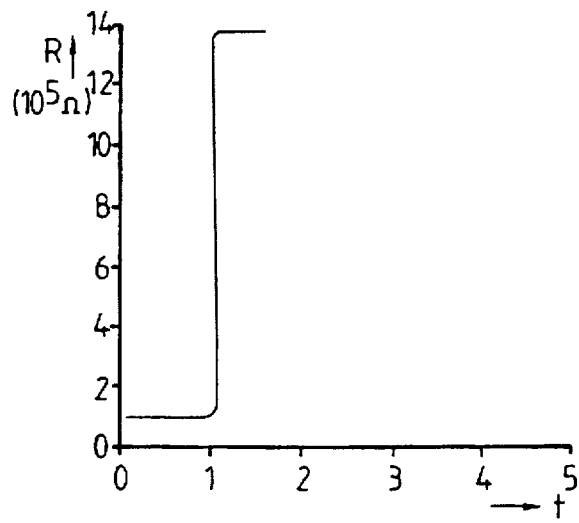

This type of behaviour can be observed in the FIGS. 4 ($SnO_2$) and 5 ($In_2O_3$) upon heavy combustion, such as for example paper with flames. When these two detectors are submitted to the same fire box, it appears that the global resistance of the captors greatly increases upon combustion.

However it should be noted that the resistance of the detector realised with the tin oxide powder (FIG. 4) started by decreasing before increasing.

This type of behaviour clearly shows that the Fermi level is unique for each semiconductor powder. Consequently, a given gas produced in an oxidation chain and presenting a donor behaviour with for example tin oxide can inversely present an acceptor behaviour for a captor formed by titan oxide.

This can be explained by the fact that the gases produced upon combustion of a compound as simple as methane undergo a series of intermediary stages.

Thus, in this case we obtain:

$$CH_4 \xrightarrow{O_2} CH_3OH \xrightarrow{O_2} CH_2O \xrightarrow{O_2}$$

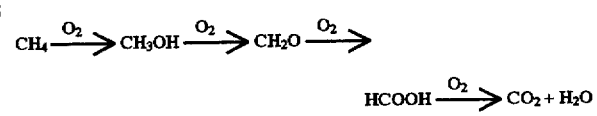

Whether the combustion is heavy or moderate, the oxidation is complete or stops at one of the intermediary stages.

This results in that depending on the Fermi level of the semiconductor element used, one of these gases, for example in the chosen case formaldehyde $CH_2O$ can manifest a donor character or not.

This signifies that, in the preceding example, the gases have always presented an acceptor character towards indium oxide, but not towards tin oxide which has presented a donor character during a few instants.

This fact is extremely important because the mixture of these powders that applies during the method according to the invention, will precisely enable to determine the level at which the detector will react with a donor or an acceptor character. According to the application aimed at, the choice and the weighting of the semiconductor powders used are adapted in order to obtain the desired response.

Thus, certain detectors destined, for example, for fire detection will be composed of a mixture of semiconductor powders of the n type, but if the action of certain agents is to be decreased some semiconductor of the p type can de added. Such adjunctions can be justified notably to avoid false alarms due for example to the presence in the atmosphere of a gas such as ammoniac which is found in certain cleaning products.

Moreover, the mixture of semiconductor powders of the n type and of the p type creates junctions p-n, n-p-n and p-n-p of the powder particles upon contact which greatly modifies the responses obtained as well in the importance of the responses than in their nature.

The life span of the captors essentially depends on the keeping in time of the specific surface of the used powders. Indeed, in time, the slight sticking effect that exists between the powder particles can progress by a slight interdiffusion due either to the presence of two powder particles of the same nature side by side, either to the action of a highly reactive gas ($NO_x$, $SO_3$, . . . ) either to the action of the voltage imposed to its terminals. This more important sticking modifies the specific surface of the powders and thus decreases the importance of their response. This is solved by increasing to a maximum the number of different substances present in the semiconductor element. Indeed, when the neighbouring powder particles are not of the same nature, the risk of seeing the sticking progress greatly decreases.

Figure 6:
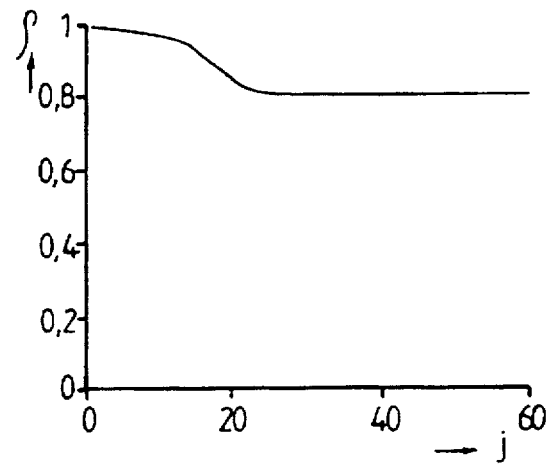
FIG. 6 shows the sensibility (ρ) of a semiconductor element according to the invention.

The heterogeneous character of the applied suspension on the substrate according to the invention also contributes to sensibly decrease this sintering effect over time. The use of powder particles of different substances reduces the interaction between these substances. For this same reason, powders constituted of inert material on the chemical and electrical plane such as silica, alumina or talc are also introduced in the mixture. The introduction of these inert powders in the mixture keeps the sticking from progressing month after month and allows to maintain the sensibility ($\rho$) of the captors, as illustrated in FIG. 6 where the time (t) is expressed in days. These inert powders have an electrical insulating character and consequently their introduction in the mixture increases the electrical resistance to the terminals of the captor. Again, the proportions and the size grading of the powders used must be chosen with care.

The detectors comprising a semiconductor element according to the invention can be used in different applications where the sudden appearance of a particular gaseous constituent in the atmosphere has to be detected. This is notably the case within the framework of fire detection because these detectors allow the detection of every type of normalised fires.

Since the detectors function at ambient temperature, it is not necessary to heat them, which considerably reduces their energy consumption, since the power of the set-up is of approximately 0.2 mW.

With respect to the use of detectors that would only use one semiconductor of the p type, the contribution is also very important, since the latter could not be used to answer the standards in force. Indeed, the combustion chambers used by the organisations that effectuate these standardisations have already been used to effectuate a very great number of fires. Consequently these chambers are covered by soot and thus strongly smell smoke. This odour is due to gas emanations that correspond to cold smoke and thus to gas reducers.

The semiconductors of the p type (for example phthalocyanine) present a resistance that highly increases in presence of such gases. This increase is so important ($R>10^{11}$ $\Omega$) that the usual electronics are no longer capable to face it and that they directly switch over to alarm upon introduction in the chamber.

The situation is completely different with a semiconductor element of the n type according to the invention, since the resistances decrease when they are introduced therein and consequently they are even more easily measurable.

Analogous captors and the electronics described are also suitable for the detection of combustion gases or certain noxious gases that appear in the atmosphere for example upon pollution.

That is the reason why they perfectly suit for the automatic regulation of ventilations in general. Amongst them, can be notably cited:
the regulation of outside air admission in the passenger spaces of automobile vehicles,
the regulation of the ventilation in toilets,
the regulation of the ventilation in parkings and tunnels,
the detection of noxious gas leaks such as chlorine $Cl_2$, hydrochloric acid HCl, cyanohydric acid HCN, sulphydric acid $H_2S$, azote oxides $NO_x$, sulphur oxides $SO_x$, ammonia $NH_3$, organic acids (formic, acetic, etc. . . . ), etc. . . .

The fact that they are susceptible of detecting the presence of gases such as trimethylamine would also enable to use them for example to indicate the state of freshness of fish. Indeed, in this case, emanations of trimethylamine are detected.

Also, their sensibility to sulphydric acid $H_2S$, shows that they can detect the presence of —SH groupments, i.e. of mercaptans. They could consequently be notably used for the detection of the presence of truffles.

Finally, the fact that these detectors present different responses according to the nature of the combustion gases enables to use them for the regulation of burners or internal combustion motors.

Figure 7:
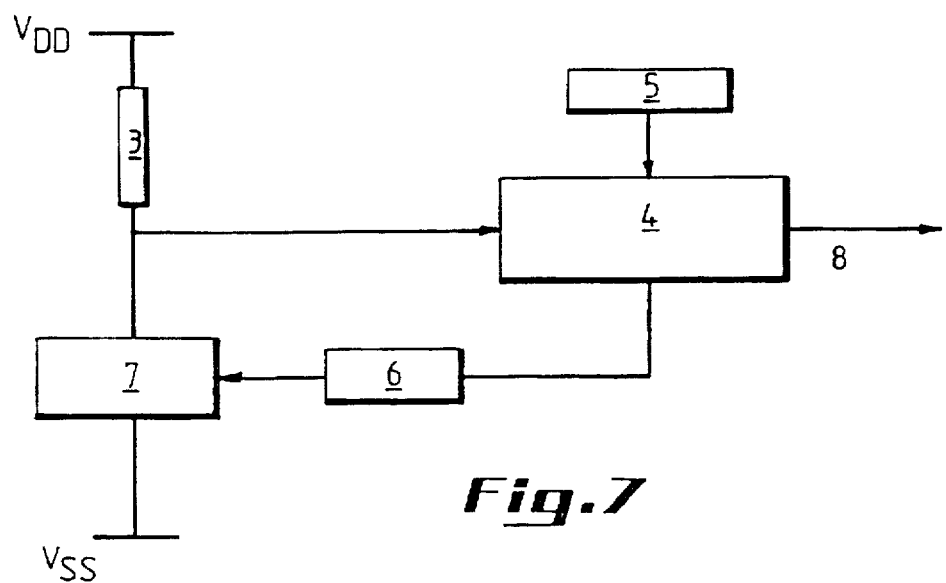
FIG. 7 shows an example of embodiment of a detector according to the invention.

FIG. 7 shows an example of an embodiment of a detector according to the invention. The detector comprises the semiconductor element 3, represented by a resistance, serially mounted with an adjustment module 7. The connection between the element 3 and the module 7 is connected to a verification and processing unit 4 whereof the input is connected to a reference signal generator 5. An output of the unit 4 is connected via a delay element 6 to a control input of the adjustment module 7.

The adjustment module 7 is intended to compensate the feeble variations in time of the resistance of the semiconductor element 3. On the other hand, a rapidly varying resistance of the semiconductor element is detected by the verification unit 4 and provokes the generation of an output signal presented at the output 8 of the unit. The adjustment module 7 is, for example, composed of a variable resistance, a bipolar transistor, FET or another impedance regulating unit, in order to maintain the voltage relatively constant at the terminals of the semiconductor element 3.

When the voltage at the terminals of the semiconductor element 3 decreases or increases slightly due to a change in the semiconductor element's resistance, this change is detected by the verfication unit 4. The verification unit 4 will produce a first or a second adjustment signal that will be presented to the adjustment module 7. Under control of the first or a second adjustment signal the impedance of the adjustment module 7 will be increased or decreased in order to maintain the sum of the impedance formed by the element 3 and the module 7 substantially constant. The adjustment signal is transmitted with a delay T to the module 7, imposed by the delay element 6.

The verification and control unit can be formed by an operational amplifier of which an input is connected to a reference voltage source and the output to a resistance bridge, itself connected to a circuit comprising a charge resistance and a discharge resistance each connected to a diode. According to an alternative embodiment the resistance bridge is connected to two reversed biased diodes, that used in their zone at constant voltage enables a charge and discharge of a capacitor.

Preferably, the adjustment module is formed by a transistor and a capacitor connected in parallel with the emitter and the collector of the transistor.

The verification and control unit can also be equipped with a microprocessor provided to produce said adjustment signals. An analog to digital conversion unit is then connected between the semiconductor element and the microprocessor.

I claim:
1. A method for manufacturing an element formed by semiconductor(s) for detecting a gas produced by combustion comprising:

(a) dispersing a first semiconductor metal oxide substance and a second semiconductor organic substance in a solvent to obtain a heterogeneous suspension where said first and second semiconductor substances are dispersed in a powder state insoluble in said solvent without being submitted to sintering;

(b) applying said heterogeneous suspension, wherein the granular state of said substances is maintained, on an insulating substrate having a specific resistivity value of at least $10^{12}$ Ω cm; and (c) removing said solvent.

2. The method for manufacturing an element formed by semiconductor(s) according to claim 1, wherein said first semiconductor formed by said semiconductor metal oxide is of the n and p type in order to form n-p-n or p-n-p junctions.

3. The method for manufacturing an element formed by semiconductor(s) according to claim 1 or 2, wherein said first semiconductor is a metal oxide wherein the metal is selected from the group consisting of tin, indium, cobalt, copper, antimony, germanium, gallium, nickel, chrome, zinc and titanium, and said second semiconductor substance is a porphyrin.

4. The method according to claim 3, wherein said porphyrin is a phthalocyanine.

5. The method for manufacturing an element formed by semiconductor(s) according to claim 1 or 2, further comprising dispersing in said solvent, a semiconductor substance formed by inert alumina or silica.

6. The method for manufacturing an element formed by semiconductor(s) according to claim 5, wherein the proportion of said inert alumina or silica in said heterogeneous suspension is determined beforehand.

7. The method for manufacturing an element formed by semiconductor(s) according to claim 1, wherein said second semiconductor formed by said semiconductor organic substance is of the n and p type in order to form n-p-n or p-n-p junctions.

8. The method for manufacturing an element formed by semiconductor(s) according to claim 2 or 7, wherein the proportion of type n, type p in said first and second semiconductor substances is determined beforehand.

9. The method for manufacturing an element formed by semiconductor(s) according to claim 1 wherein prior to dispersing, said semiconductor substances are reduced in size by grinding to less than 100 μm.

10. The method for manufacturing an element formed by semiconductor(s) according to claim 1, wherein after dispersing said first and second semiconductor substances in the solvent, the thus obtained heterogeneous suspension is submitted to intense agitation.

11. The method for manufacturing an element formed by semiconductor(s) according to claim 1, and further repeating steps (b) and (c) to form multiple layers.

12. A combustion gas detector, comprising an element composed of semiconductor(s) obtained by the method according to claim 1, which is serially mounted with an adjustment module and is connected to a verification unit provided for detecting an amount of variation of resistivity value of said element formed by semiconductor(s) and to generate an output signal after detection of a further amount of variation superior to a predetermined threshold.

13. The gas detector according to claim 12, wherein said verification unit comprises a microprocessor provided for producing an adjustment signal in response to a voltage change measured over terminals of said element formed by semiconductor(s).

14. The gas detector according to claim 13, wherein said adjustment module comprises a transistor and a capacitor connected in parallel, said adjustment signals being supplied at the base of said transistor.

* * * * *